(12) United States Patent
Yang et al.

(10) Patent No.: US 11,760,995 B2
(45) Date of Patent: *Sep. 19, 2023

(54) PCR PRIMER PAIR AND APPLICATION THEREOF

(71) Applicant: MGI TECH CO., LTD, Shenzhen (CN)

(72) Inventors: Lin Yang, Shenzhen (CN); Ya Gao, Shenzhen (CN); Guodong Huang, Shenzhen (CN); Yicong Wang, Shenzhen (CN); Yuqian Wang, Shenzhen (CN); Yanyan Zhang, Shenzhen (CN); Fang Chen, Shenzhen (CN); Na Zhong, Shenzhen (CN); Hui Jiang, Shenzhen (CN); Xun Xu, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 326 days.

This patent is subject to a terminal disclaimer.

(21) Appl. No.: 16/624,791

(22) PCT Filed: Jun. 20, 2017

(86) PCT No.: PCT/CN2017/089195
§ 371 (c)(1),
(2) Date: Dec. 19, 2019

(87) PCT Pub. No.: WO2018/232594
PCT Pub. Date: Dec. 27, 2018

(65) Prior Publication Data
US 2020/0131510 A1   Apr. 30, 2020

(51) Int. Cl.
| C12N 15/10 | (2006.01) |
| C12Q 1/68 | (2018.01) |
| C12Q 1/6853 | (2018.01) |
| C12Q 1/686 | (2018.01) |

(52) U.S. Cl.
CPC ......... *C12N 15/1093* (2013.01); *C12Q 1/686* (2013.01); *C12Q 1/6853* (2013.01)

(58) Field of Classification Search
CPC ... C12N 15/1093; C12Q 1/6853; C12Q 1/686
See application file for complete search history.

(56) References Cited

U.S. PATENT DOCUMENTS

| 2003/0050470 A1* | 3/2003 | An | C07H 21/00 435/6.14 |
| 2006/0281092 A1* | 12/2006 | Wille | C12Q 1/6809 977/924 |
| 2006/0292611 A1* | 12/2006 | Berka | C12N 15/1093 435/6.1 |
| 2009/0130720 A1 | 5/2009 | Nelson et al. | |
| 2011/0159505 A1* | 6/2011 | Carnichi | C12Q 1/6848 435/6.12 |
| 2014/0113332 A1* | 4/2014 | Betts | C12Y 207/07007 536/23.1 |
| 2020/0216838 A1* | 7/2020 | Yang | C12Q 1/6806 |
| 2020/0216874 A1* | 7/2020 | Yang | C12Q 1/6806 |

FOREIGN PATENT DOCUMENTS

| CN | 102952895 A | 3/2013 | |
| CN | 103820561 B | 4/2016 | |
| CN | 106282173 A | 1/2017 | |
| WO | 0185988 A1 | 11/2001 | |
| WO | WO-2011142861 A2 * | 11/2011 | ............ C12P 19/34 |
| WO | 2011142861 A9 | 3/2012 | |
| WO | WO-2015117040 A1 * | 8/2015 | ............ C12N 15/66 |
| WO | WO-2018232594 A1 * | 12/2018 | ......... C12N 15/1093 |

OTHER PUBLICATIONS

Korfhage, C., Fricke, E., Meier, A., Geipel, A., Baltes, M., Krüger, N., Herschel, F. and Erbacher, C., 2017. Clonal rolling circle amplification for on-chip DNA cluster generation. Biology Methods and Protocols, 2(1) pp. 1-10. (Year: 2017).*
Garcia-Nafria, J., Watson, J.F. and Greger, I.H., 2016. IVA cloning: a single-tube universal cloning system exploiting bacterial in vivo assembly. Scientific reports, 6(1), pp. 1-12. (Year: 2016).*
Garcia-Nafria et al., 2016. Scientific reports, Supplementary pp. 1-6. (Year: 2016).*
Zeng et al., 2017. A restriction-free method for gene reconstitution using two single-primer PCRs in parallel to generate compatible cohesive ends. BMC biotechnology, 17(1), pp. 1-7. (Year: 2017).*
Zeng et al., 2017. BMC biotechnology, 17(1), pp. 1-7. Supplementary TableS1, primer sequences. pp. 1-5 (Year: 2017).*
Putney et al., 1981. A DNA fragment with an alpha-phosphorothioate nucleotide at one end is asymmetrically blocked from digestion by exonuclease III and can be replicated in vivo. Proceedings of the National Academy of Sciences, 78(12), pp. 7350-7354 (Year: 1981).*
Vosberg, H.P. and Eckstein, F., 1982. Effect of deoxynucleoside phosphorothioates incorporated in DNA on cleavage by restriction enzymes. Journal of Biological Chemistry, 257(11), pp. 6595-6599. (Year: 1982).*

(Continued)

*Primary Examiner* — Samuel C Woolwine
*Assistant Examiner* — Olayinka A Oyeyemi
(74) *Attorney, Agent, or Firm* — Westman, Champlin & Koehler, P.A.; Z. Peter Sawicki; Amanda M. Prose

(57) ABSTRACT

Provided is a PCR primer pair, comprising: a first primer and a second primer, wherein the first primer comprises a first specific sequence and a first random sequence; the first specific sequence is located on 3' end of the first primer, and the first random sequence is located on 5' end of the first primer; the second primer comprises a second specific sequence and a second random sequence, the second specific sequence is located on 3' end of the second primer, and the second random sequence is located on 5' end of the second primer; moreover, the first specific sequence and the second specific sequence are an upstream primer and a downstream primer directed to a target sequence respectively, and the first random sequence and the second random sequence are inverse complementary.

16 Claims, 5 Drawing Sheets

Specification includes a Sequence Listing.

(56) References Cited

OTHER PUBLICATIONS

Nikiforov et al., 1994. The use of phosphorothioate primers and exonuclease hydrolysis for the preparation of single-stranded PCR products and their detection by solid-phase hybridization. Genome Research, 3(5), pp. 285-291. (Year: 1994).*
SantaLucia Jr, John. Physical principles and visual-OMP software for optimal PCR design. PCR Primer Design. Humana Press, 2007: pp. 3-33. (Year: 2007).*
International Search Report and Written Opinion issued for PCT/CN2017/089195, dated Feb. 22, 2018.
Search Report issued for EP patent application 17915186.5, dated Dec. 7, 2020.
Korfhage, C. "Clonal rolling circle amplification for on-chip DNA cluster generation" (2017) Biology Methods and Protocols, vol. 2, No. 1.

* cited by examiner

PCR PRIMER PAIR AND APPLICATION THEREOF

CROSS REFERENCE TO RELATED APPLICATIONS

This application is a US national phase application based upon PCT Application No. PCT/CN2017/089195 filed on Jun. 20, 2017, the entire content of which is incorporated herein by reference.

FIELD

The present disclosure relates to the field of biotechnology, in particular to PCR amplification, and more particular to PCR primer pair and application thereof.

BACKGROUND

Polymerase Chain Reaction (PCR) established by Mullis in 1983 has become a classical experimental method in molecular biology and related fields. Its application has been diversified, from gene amplification and gene detection, to gene cloning, genetic engineering, genetic analysis and the like, which even extends to non-biological areas. With the development in recent years, this technology itself has been improving, with continuously improved reliability. Meanwhile, a series of new concepts and experimental methods have been developed based on this basic principle of PCR, which has important application value in life science research.

Primers are one of the key factors in all PCR methods and technologies. Primer designs are currently available through computer and network. The advantages of online primer design include 1) no need to be proficient in software operation; and 2) simultaneous analysis of many variables. However, good primers designed by conventional primer design software do not definitely produce good results in practical working, especially for templates containing high GC regions and sequences similar to other regions, thus ultimately resulting in poor specificity for the product amplified in the presence of the primers, as well as poor PCR amplification efficiency. In addition, the primers with optimization for these regions usually cannot get satisfactory results.

Therefore, the existing conventional PCR primer design method still needs to be improved.

SUMMARY

The present disclosure aims to at least solve one of the technical problems existing in the prior art. For this purpose, an object of the present disclosure is to propose a PCR primer design strategy and a corresponding PCR primer pair which can effectively reduce GC bias during PCR amplification and improve amplification specificity.

First, it should be noted that the present disclosure has been completed based on the following findings of present inventors.

There are various websites and software available online for free services of online primer design, such as NetPrimer. Lots of different primer design stand-alone software has been commonly used, with their own advantages. For example, Rightprimer™ (Bio2Disk), which has excellent proofreading function, can find out primers having highly strong specificity to sequences to be amplified in a short time by searching Genebank and aligning possible primers with background DNAs. Oligo™ (Molecular Biology Insights, Inc.) is suitable for designing primers for Multiplex PCR and Consensus PCR, and can provide suitable PCR conditions. PrimerPremier (or Premierbiosoft) can design primers according to protein sequences in the case of unknown nucleic acid sequences, which can be especially useful in cloning new genes when only part of protein sequences are known. PrimerDesigner210 (Scientific and Educational Software) is widely used due to its small size and complete functionality.

However, good primers designed by conventional primer design software do not definitely produce good results in practical working, especially for templates containing high GC regions and sequences similar to other target regions, thus ultimately resulting in poor specificity for the product amplified in the presence of the primers, as well as poor PCR amplification efficiency. In addition, the primers with optimization for these regions usually cannot get satisfactory results.

The present inventors after research have found that current PCR primers are required to be designed according to strict primer design conditions. PCR specificity and amplification efficiency greatly depend on the quality of primer designed, thus the primers generally cannot get good results in some repeat regions, high GC regions or regions with advanced structures, thereby plenty of energy and resources will cost for primer design and optimization. The present inventors have conducted a series of design and experimental explorations to solve the problems. Moreover, it is surprisingly discovered by the present inventors that such problems can be effectively addressed by addition of a pair of complementary sequences at the 5' ends of a conventional primer pair thus forming a primer pair with a stable primer-dimer structure which is reversely complement at the 5' end and overhanging at the 3' end.

Further, in a first aspect, the present disclosure in embodiments provides a PCR primer pair. In embodiments of the present disclosure, the PCR primer pair comprises a first primer and a second primer, wherein the first primer comprises a first specific sequence and a first random sequence, and the second primer comprises a second specific sequence and a second random sequence, wherein the first specific sequence is located at the 3' end of the first primer and the first random sequence is located at the 5' end of the first primer, the second specific sequence is located at the 3' end of the second primer and the second random sequence is located at the 5' end of the second primer, the first specific sequence and the second specific sequence are respectively an upstream primer and a downstream primer for a target sequence, and the first random sequence and the second random sequence are reversely complementary. The present inventors have surprisingly found that the PCR primer pair of the present disclosure can effectively reduce the GC bias during PCR amplification, thus increasing amplification specificity. Specifically, use of conventional primers will result in GC bias to some extent during PCR amplification of the next-generation sequencing library, but the PCR primer pair of the present disclosure (sometimes referred to as "Padlock Primer") is capable of effectively reducing the GC bias during library PCR amplification.

In embodiments of the present disclosure, the first specific sequence and the second specific sequence each have a TM value of 55-65° C., and the first primer and the second primer each have a TM value of 65-75° C. Thus, the PCR reaction is subjected to a first round of linear amplification under a low annealing temperature of 55-65° C., followed by a second round of circular amplification under a high annealing temperature of 65-72° C. in subsequent cycles. During the circular amplification, the specific sequence of primers cannot bind to the specific site of templates directly because the specific sequence has a TM value of 55-65° C. which is lower than the high annealing temperature of circular amplification. Such a circular amplification can be effectively performed only when the 5' end and the 3' end of the padlock primer bind to the 5' end and the specific site of templates respectively, i.e. performing the circular amplification through two recognition-site binding.

The PCR primer pair of the present disclosure is suitable for PCR amplification and library construction for any form of DNA sample to be tested. It should be noted that the "DNA sample to be tested" described in the present disclosure is somewhat different from the conventional understanding which does not include treated DNA. However, in the present disclosure, the "DNA sample to be tested" may include both treated DNA and untreated DNA. Generally, during construction of sequencing library, the genomic DNA of sample will be fragmented and added with adaptors for sequencing, thus obtaining DNA fragments carrying sequencing adaptors corresponding to a sequencing platform, which will be subjected to subsequent amplification and other steps for obtaining sequencing products. Such a DNA fragment carrying sequencing adaptor corresponding to a sequencing platform is called as the "treated DNA". Correspondingly, DNA fragments which are not treated according to the method as described above are called the "untreated DNA". If the PCR primer pair of the present disclosure is for untreated DNA, specific target fragments can be amplified; but if the PCR primer pair of the present disclosure is for treated DNA, whole genomic DNA fragments can be amplified.

In some embodiments of the present disclosure, when the DNA sample to be tested is the treated DNA which carries a universal sequence, such as a sequencing adaptor, the first specific sequence and the second specific sequence have to specifically recognize a target sequence carrying the universal sequence accordingly, that is, the target sequence actually consists of a universal sequence and a target region sequence, in which the "universal sequence" herein means a sequence complement with the specific sequence of the PCR prime pair, including adaptor sequence for a sequencing platform, i.e. a sequencing adaptor. When the DNA sample to be tested is DNA fragments which do not carry a universal sequence, i.e. templates for PCR reaction, the first specific sequence and the second specific sequence have to specifically recognize the target sequence accordingly. Meanwhile, if a sequencing library is required, adaptor sequence for sequencing (i.e. a universal sequence) can be inserted into the first primer and the second primer respectively or between the specific sequence and the random sequence, so that PCR amplification products can be ligated with adaptors, thus can be effectively used in sequencing platforms.

In further embodiments of the present disclosure, at least one of the first primer and the second primer further comprises a tag sequence, by which a plurality of samples can be subjected to PCR amplification simultaneously, and the samples can be distinguished by corresponding tag sequences. The position of the tag sequence in the first primer and the second primer is not particularly limited as long as the tag sequence can distinguish different samples without affecting PCR amplification. According to some specific examples of the present disclosure, the tag sequence may be located between a specific sequence and a random sequence, by which a first tag sequence may be arranged between the first specific sequence and the first random sequence of the first primer, and/or a second tag sequence may be arranged between the second specific sequence and the second random sequence of the second primer. According to another embodiment of the present disclosure, the tag sequence may also be arranged within the random sequence, i.e. forming a part of the random sequence, by which, exhibiting the function of distinguishing different samples without affecting PCR amplification as well.

In embodiments of the present disclosure, the first random sequence and the second random sequence each have a length of 15-45 bp, and the first specific sequence and the second specific sequence each have a length of 15-30 bp.

In embodiments of the present disclosure, the $1-5^{th}$ bases from each of the 5' end and the 3' end of the first primer are respectively subjected to modification, and the $1-5^{th}$ bases from each of the 5' end and the 3' end of the second primer are respectively subjected to modification, so as to effectively prevent from cleavage by exonuclease. According to some specific examples of the present disclosure, the $1-5^{th}$ bases from each of the 5' end and the 3' end of the first primer are respectively subjected to thio-modification, and the $1-5^{th}$ bases from each of the 5' end and the 3' end of the second primer are respectively subjected to thio-modification.

In some embodiments of the present disclosure, the type of thio-modification is not particularly limited as long as the first primer and the second primer can be prevented from cleavage by exonuclease, such as degradation by 5-3' exonuclease or 3-5' exonuclease. According to some specific examples of the present disclosure, the thio-modification is any one selected from phosphorothioate modification, methyl-sulfate modification and peptide nucleic acid modification.

In an embodiment of the present disclosure, at least one of the first primer and the second primer is subjected to phosphorylation modification at the 5' end. Thus, the products obtained by using the PCR primer pair of the present disclosure, which is a loop-like substance with a nick (that is, the 5' end and the 3' end of the loop-like substance are not connected) can be ligated by a ligase so as to form complete circular DNA.

In a second aspect, the present disclosure in embodiments provides a PCR amplification kit. In embodiments of the present disclosure, the kit comprises the PCR primer pair as described above. In embodiments of the present disclosure, using the kit comprising the PCR primer pair of the present disclosure for PCR amplification, can bring low GC bias, high amplification specificity and excellent amplification effect during amplification, compared to conventional primers.

In a third aspect, the present disclosure in embodiments provides a method for PCR amplification. In embodiments of the present disclosure, the method performs the PCR amplification by using the PCR primer pair or the PCR amplification kit as described above. Thus, PCR amplification of templates can be effectively achieved through this method. Moreover, the method is capable of increasing specificity of PCR amplification, effectively reducing generation of non-specific products, and improving amplification efficiency.

In an embodiment of the present disclosure, the method comprises two rounds of amplification. In the first round of amplification, the PCR primer pair and a template are subjected to linear amplification under an annealing temperature of 55-65° C., and in the second round of amplification, a product of the linear amplification is subjected to circular amplification under an annealing temperature of 65-72° C. Thus, starting from the second PCR cycle (i.e.

circular amplification in the second round), bases at the 5' end of the first primer or the second primer can reversely complement with bases at the 5' end of the newly-generated template, and the specific sequence at the 3' end of the first primer or the second primer can reversely complement with bases at the 3' end of the newly-generated template, that is, two recognition sites for binding between primer and template (referring to FIG. 3), thus increasing specificity of PCR amplification, and effectively decreasing the generation of non-specific products.

In an embodiment of the present disclosure, the two rounds of amplification are performed as the following amplification reaction procedure:

| | |
|---|---|
| step 1 | preheating for 2 minutes at 98° C. |
| step 2 | denaturing for 10 seconds at 98° C. |
| step 3 | annealing for 2 minutes at 55-65° C. |
| step 4 | amplifying for 30 seconds at 72° C. |
| step 5 | denaturing for 10 seconds at 98° C. |
| step 6 | annealing for 1 minute at 65-72° C. |
| step 7 | repeating steps 5 and 6 for 5-35 circles |
| step 8 | extending for 5 minutes at 72° C. |

Therefore, the GC bias during PCR amplification is low, the amplification specificity is high and the amplification effect is excellent.

In a fourth aspect, the present disclosure in embodiments provides a method for preparing a circular DNA library. In embodiments of the present disclosure, the method comprises the steps of:

(1) subjecting a DNA sample to be tested to PCR amplification according to the method for PCR amplification as described above, so as to obtain an amplification product comprising a loop-like substance, wherein the 5' end and the 3' end of the loop-like substance are not connected,
at least one of the first primer and the second primer is subjected to phosphorylation modification at the 5' end,
the 1-5$^{th}$ bases from each of the 5' end and the 3' end of the first primer are respectively subjected to thio-modification,
the 1-5$^{th}$ bases from each of the 5' end and the 3' end of the second primer are respectively subjected to thio-modification, and (2) subjecting the amplification product comprising the loop-like substance to a ligation reaction by using a ligase, such that the 5' end and the 3' end of the loop-like substance are ligated, thus forming circular DNAs, the circular DNAs constituting the circular DNA library,
wherein the circular DNA library is a single-stranded circular DNA library when either of the first primer and the second primer is subjected to phosphorylation modification at the 5' end; and the circular DNA library is a double-stranded circular DNA library when both the first primer and the second primer are subjected to phosphorylation modification at the 5' end.

In embodiments of the present disclosure, a single-stranded circular DNA library or a double-stranded circular DNA library can be efficiently prepared through the method. The obtained single-stranded circular DNA library or double-stranded circular DNA library is of good library quality, which exhibits good effect for DNA preservation or library sequencing.

In embodiments of the present disclosure, the method further comprises: (3) removing linear DNAs. Thus, the obtained library is of good quality.

In some specific examples of the present disclosure, the linear DNAs are removed through a linear-chain digestion reaction.

In embodiments of the present disclosure, the DNA sample to be tested in the step (1) is added with universal sequence at the 5' end and the 3' end respectively.

In embodiments of the present disclosure, the PCR primer pair of the present disclosure and use thereof have at least one of the following advantages:

1. The design strategy of the PCR primer pair of the present disclosure simplifies the primer design flow and optimizes the experimental steps. Each primer of the primer pair consists of a specific sequence at the 3' end and a random sequence (i.e. a complementary sequence) at the 5' end, thus the forward primer and the reverse primer form a stable dimer structure through complementary sequences, which does not need to meet strict conditions as conventional primers, thus greatly simplifying the design process. During conventional primer design, complementation of the 5' end and the 5' end of primers, generation of palindrome structure via primer itself and the like are necessarily to be avoided so as to ensure that no dimer structure is formed between primers and no self-extension of primers occurs for PCR. However, for designing the PCR primer pair of the present disclosure, such problems are not necessary to be considered, because the padlock primer is of a stable dimer structure, of which the 5' ends are complementary with each other and the 3' ends can complement with specific sequences and extend normally; in contrast, for a conventional primer pair, if its 5' ends are complementary with each other, its 3' ends will have no enough sequence to complement with specific sequences of templates. Moreover, the complementary sequences at the 5' end formed between two primers of the padlock primer pair of the present disclosure display potential energy which is greatly stronger than that of self-palindrome structure, thus the dimer structure at the 5' end is preferably formed even the 5' end and the 3' end have sequences complementary with each other.

2. The PCR amplification method of the present disclosure can increase specificity of PCR amplification, thus effectively reducing generation of non-specific products. Starting from the second PCR cycle, bases at the 5' end of the primer (i.e. the random sequence) can reversely complement with bases at the 5' end of the newly-generated template, and the specific sequence at the 3' end of the primer can reversely complement with bases at the 3' end of the newly-generated template, that is, two recognition sites for binding between primer and template (refer to FIG. 3), thus significantly increasing binding ability between primer and template, and amplification specificity. Further, amplification efficiency is also effectively improved due to the increased binding ability.

3. Using the PCR primer pair of the present disclosure for PCR amplification can effectively reduce GC bias of different templates in amplification of sequencing libraries (especially, the next-generation sequencing library), because effective PCR amplification is only carried out after denaturation of template and binding of primer to template. The GC bias is generated because templates containing some high GC regions would have renatured rapidly before the primer binds to the template during PCR, thus these high GC regions cannot be efficiently amplified. For the padlock primer of the present disclosure, two recognition sites for binding primer to template are presented, which can greatly improve the binding ability between primer and template, thereby the padlock primer can be effectively paired with templates containing high GC regions, thus reducing the GC bias.

4. The products obtained by the PCR amplification method of the present disclosure are loop-like substances with a nick (that is, the 5' end and the 3' end of the loop-like substance are not connected), thus for experiments where the products have to be cyclized, the cyclization can be realized by addition of a ligase, without complex denaturation, quenching and the like steps, thereby effectively simplifying the experimental process.

Additional aspects and advantages of the present disclosure will be given in the following description partly, part of which will become apparent from the following description or be acknowledged through the practice of the present disclosure.

BRIEF DESCRIPTION OF THE DRAWINGS

The above and/or additional aspects and advantages of the present disclosure will become apparent and easily understood from the description of the embodiments in combination with the following drawings, in which.

DETAILED DESCRIPTION

Figure 1:
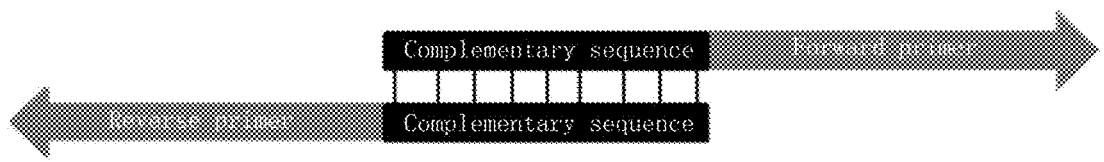
FIG. 1 is a schematic diagram showing the structure of a PCR primer pair (i.e. a padlock primer) of the present disclosure according to an embodiment of the present disclosure.

Embodiments of the present disclosure are described in detail below, examples of which are illustrated in the accompanying drawings. The embodiments described below with reference to the accompanying drawings are intended to be illustrative and for explanation of the present disclosure, which cannot be construed as limiting.

It should be noted, the terms "first" and "second" are used for purposes of description and are not intended to indicate or imply relative importance or significance or impliedly indicate quantity of the technical feature referred to. Thus, the feature defined with "first" and "second" may comprise one or more this feature either explicitly or implicitly. Further, in the description of the present disclosure, "a plurality of" means two or more than two, unless specified otherwise.

PCR Primer Pair

In a first aspect, the present disclosure in embodiments provides a PCR primer pair. According to embodiments of the present disclosure, the PCR primer pair comprises a first primer and a second primer, in which, the first primer comprises a first specific sequence and a first random sequence, and the second primer comprises a second specific sequence and a second random sequence, in which the first specific sequence is located at the 3' end of the first primer and the first random sequence is located at the 5' end of the first primer, the second specific sequence is located at the 3' end of the second primer and the second random sequence is located at the 5' end of the second primer, the first specific sequence and the second specific sequence are respectively an upstream primer and a downstream primer for a target sequence, and the first random sequence and the second random sequence are reversely complementary. The present inventors have surprisingly found that the PCR primer pair of the present disclosure can effectively reduce the GC bias during PCR amplification, thus increasing amplification specificity. Specifically, use of conventional primers will result in GC bias to some extent during PCR amplification of the next-generation sequencing library, but the PCR primer pair of the present disclosure (sometimes referred to as "Padlock Primer") is capable of effectively reducing the GC bias during library PCR amplification.

It should be noted that the "first random sequence" and the "second random sequence" of the present disclosure may be unfixed or fixed sequences as long as they are reversely complementary to each other.

According to embodiments of the present disclosure, the first specific sequence and the second specific sequence each have a TM value of 55-65° C., and the first primer and the second primer each have a TM value of 65-75° C. Thus, the PCR reaction is subjected to a first round of linear amplification under a low annealing temperature of 55-65° C., followed by a second round of circular amplification under a high annealing temperature of 65-72° C. in subsequent cycles. During the circular amplification, the specific sequence of primer cannot bind to the specific site of templates directly because the specific sequence has a TM value of 55-65° C. which is lower than the high annealing temperature of circular amplification. Such a circular amplification can be effectively performed only when the 5' end and the 3' end of the padlock primer bind to the 5' end and the specific site of templates respectively, i.e. performing the circular amplification through two recognition-site binding.

The PCR primer pair of the present disclosure is suitable for PCR amplification and library construction for any form of DNA sample to be tested. It should be noted that the "DNA sample to be tested" described in the present disclosure is somewhat different from the conventional understanding which does not include treated DNA. However, in the present disclosure, the "DNA sample to be tested" may include both treated DNA and untreated DNA. Generally, during construction of sequencing library, the genomic DNA of sample will be fragmented and added with adaptor for sequencing, thus obtaining DNA fragments carrying sequencing adaptors corresponding to a sequencing platform, which will be subjected to subsequent amplification and other steps for obtaining sequencing products. Such a DNA fragment carrying sequencing adaptor corresponding to a sequencing platform is called as the "treated DNA". Correspondingly, DNA fragments which are not treated according to the method as described above are called the "untreated DNA". If the PCR primer pair of the present disclosure is for untreated DNA, specific target fragments can be amplified; but if the PCR primer pair of the present disclosure is for treated DNA, whole genomic DNA fragments can be amplified.

According to some embodiments of the present disclosure, when the DNA sample to be tested is the treated DNA which carries a universal sequence, such as a sequencing adaptor, the first specific sequence and the second specific sequence have to specifically recognize a target sequence carrying the universal sequence accordingly, that is, the target sequence actually consists of a universal sequence and a target region sequence, in which the "universal sequence" herein means a sequence complement with the specific sequence of the PCR prime pair, including adaptor sequence for a sequencing platform, i.e. a sequencing adaptor. When the DNA sample to be tested is DNA fragments which do not carry a universal sequence, i.e. templates for PCR reaction, the first specific sequence and the second specific sequence have to specifically recognize the target sequence accordingly. Meanwhile, if a sequencing library is required to be constructed, adaptor sequence for sequencing (i.e. a universal sequence) can be inserted into the random sequence or between the specific sequence and the random sequence for the first primer and the second primer respectively, so that PCR amplification products can be ligated with adaptors, thus can be effectively used in sequencing platform.

According to further embodiments of the present disclosure, at least one of the first primer and the second primer further comprises a tag sequence, by which a plurality of samples can be subjected to PCR amplification simultaneously, and the samples can be distinguished by corresponding tag sequences. The position of the tag sequence in the first primer and the second primer is not particularly limited as long as the tag sequence can distinguish different samples without affecting PCR amplification. According to some specific examples of the present disclosure, the tag sequence may be located between a specific sequence and a random sequence, by which a first tag sequence may be arranged between the first specific sequence and the first random sequence of the first primer, and/or a second tag sequence may be arranged between the second specific sequence and the second random sequence of the second primer. According to another embodiment of the present disclosure, the tag sequence may also be arranged within the random sequence, i.e. forming a part of the random sequence, by which, exhibiting the function of distinguishing different samples without affecting PCR amplification as well.

According to embodiments of the present disclosure, the first random sequence and the second random sequence each have a length of 15-45 bp, and the first specific sequence and the second specific sequence each have a length of 15-30 bp.

According to embodiments of the present disclosure, the 1-5$^{th}$ bases from each of the 5' end and the 3' end of the first primer are respectively subjected to thio-modification, and the 1-5$^{th}$ bases from each of the 5' end and the 3' end of the second primer are respectively subjected to thio-modification, so as to effectively prevent from cleavage by exonuclease.

According to some embodiments of the present disclosure, the type of thio-modification is not particularly limited as long as the first primer and the second primer can be prevented from cleavage by exonuclease, such as cleavage by 5-3' exonuclease or 3-5' exonuclease. According to some specific examples of the present disclosure, the thio-modification is any one selected from phosphorothioate modification, methyl-sulfate modification and peptide nucleic acid modification.

According to an embodiment of the present disclosure, at least one of the first primer and the second primer is subjected to phosphorylation modification at the 5' end. Thus, a loop-like substance with a nick which is obtained after two rounds of amplification (that is, the 5' end and the 3' end of the loop-like substance are not connected) can be ligated by a ligase so as to form complete circular DNA.

In addition, it should be noted, referring to FIG. 1 which shows the schematic structure of the PCR primer pair of the present disclosure, the design strategy of the PCR primer pair of the present disclosure includes addition of a pair of complementary sequences at the 5'-ends of a conventional primer pair (including a forward primer and a reverse primer), thus forming a PCR primer pair (i.e. Padlock Primer, PP) which is reversely complementary at the 5' end and overhanging at the 3' end, in which two primers of the padlock primer pair form a stable primer-dimer structure, and the complementary sequences may be unfixed or fixed sequences. The first primer and the second primer of the PCR primer pair each have a length of 30-70 bp, and have a high TM value, generally of 65-75° C. The complementary sequences (i.e. the first random sequence and the second random sequence, being unfixed or fixed sequences) at the 5'-end of the padlock primer pair each have a length of 15-45 bp. The first specific sequence and the second specific sequence at the 3'-ends of the padlock primer pair, which are complementary to target sequences of a template respectively, each have a length of 15-30 bp, and have a low TM value, generally of 55-65° C.

Figure 3:
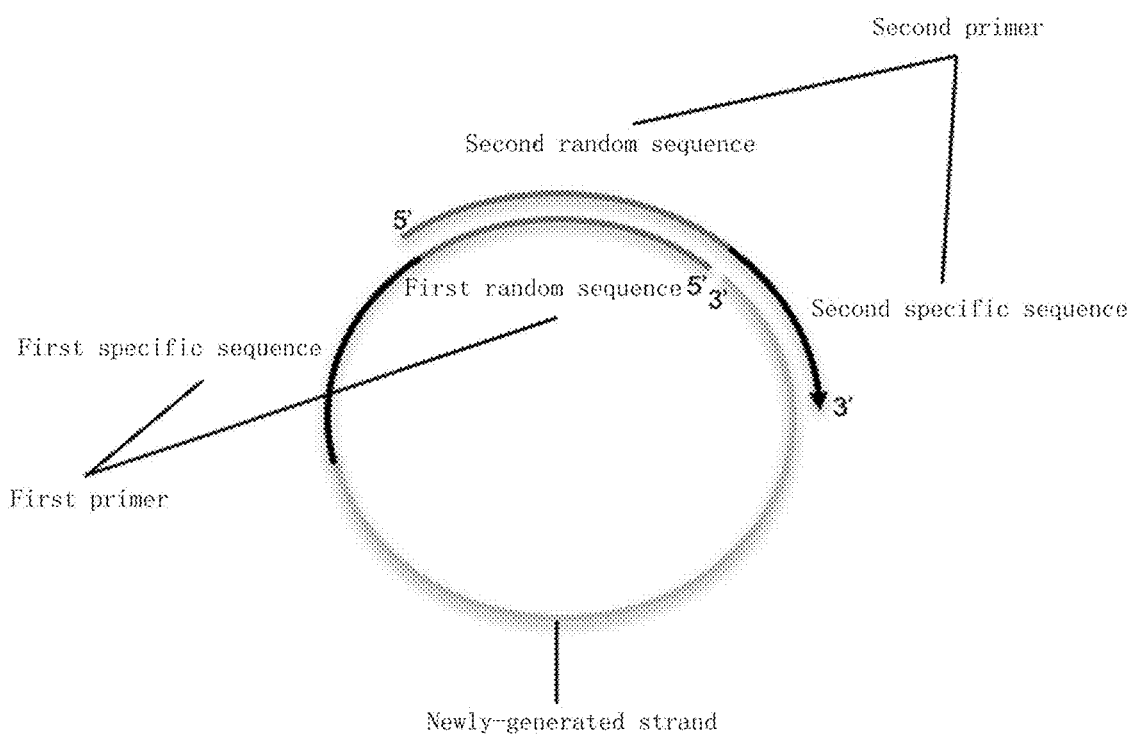
FIG. 3 is a schematic diagram showing binding between primer and newly-generated strand in the circular amplification of the present disclosure according to an embodiment of the present disclosure.

Further, for the application of the PCR primer pair of the present disclosure, the PCR primer pair of the present disclosure is subjected to two different amplification processes (i.e. two rounds of amplification) to complete the PCR amplification, referring to FIG. 3, in the first round of amplification, the annealing temperature is 55-65° C. and the cycle number is 1; and in the second round of amplification, the annealing temperature is 65-72° C. and the cycle number is 5-35. During the first round of amplification, only the specific sequence at the 3' end of the PCR primer pair can bind to template, thus the annealing temperature in this round is low. During the second round of amplification, the newly-generated template (i.e. the product of the first round of amplification) is firstly paired with the complementary sequence at the 5' end of the PCR primer pair (i.e. the first random sequence or the second random sequence), followed by pairing with the specific sequence at the 3' end (i.e. the first specific sequence or the second specific sequence), that is, two recognition sites for binding between primer and template, which greatly improved the annealing temperature of primer, resulting in a high annealing temperature.

Further, it should be noted, in the second round of amplification, the circular amplification can be effectively performed only when the 5' end and the 3' end of the primer bind to the newly-generated template simultaneously, thus both specificity of PCR amplification and binding between primer and template are greatly improved via two recognition sites, with improved PCR amplification efficiency. Therefore, using the PCR primer pair of the present disclosure for PCR amplification, is capable of significantly increasing the specificity of PCR amplification, effectively reducing the generation of non-specific products, and reducing the GC bias during amplification, compared to conventional PCR primers. Thus, use of such a primer pair in sequencing, especially in the next-generation sequencing library, can effectively reduce the genome-wide GC bias in library enrichment and amplification.

In addition, according to the embodiment of the present disclosure, the products obtained by PCR amplification in the presence of the PCR primer pair of the present disclosure can be directly cyclized by a ligation reaction, thus obtaining circular DNAs. Specifically, the products can be directly subjected to cyclization in a ligation reaction system, without additional denaturation, quenching and other steps, thus cyclization process is simplified, and the process for preparing a circular DNA library is simplified accordingly.

Application

Further, in a second aspect, the present disclosure in embodiments also provides a PCR amplification kit. According to an embodiment of the present disclosure, the kit comprises the PCR primer pair as described above. According to an embodiment of the present disclosure, using the kit comprising the PCR primer pair of the present disclosure for PCR amplification, can bring low GC bias, high amplification specificity and excellent amplification effect during amplification, compared to conventional primers.

Further, the present disclosure in embodiments proposes use of the PCR primer pair and the kit comprising the PCR primer pair.

In a third aspect, the present disclosure in embodiments provides a method for PCR amplification. According to an embodiment of the present disclosure, the method performs PCR amplification by using the PCR primer pair or the PCR amplification kit as described above. Thus, PCR amplification of template can be effectively achieved by using this method. Moreover, this method can increase specificity of PCR amplification, effectively reduce generation of non-specific products, and improve amplification efficiency.

According to an embodiment of the present disclosure, the method comprises two rounds of amplification. In the first round of amplification, the PCR primer pair and a template are subjected to linear amplification under an annealing temperature of 55-65° C., and in the second round of amplification, a product of the linear amplification is subjected to circular amplification under an annealing temperature of 65-72° C. Thus, starting from the second PCR cycle (i.e. circular amplification in the second round), bases at the 5' end of the first primer or the second primer can reversely complement with bases at the 5' end of the newly-generated template, and the specific sequence at the 3' end of the first primer or the second primer can reversely complement with bases at the 3' end of the newly-generated template, that is, two recognition sites for binding between primer and template (referring to FIG. 3), thus increasing specificity of PCR amplification, and effectively decreasing the generation of non-specific products.

According to an embodiment of the present disclosure, the two rounds of amplification are performed as the following amplification reaction procedure:

| | |
|---|---|
| step 1 | preheating for 2 minutes at 98° C. |
| step 2 | denaturing for 10 seconds at 98° C. |
| step 3 | annealing for 2 minutes at 55-65° C. |
| step 4 | amplifying for 30 seconds at 72° C. |
| step 5 | denaturing for 10 seconds at 98° C. |
| step 6 | annealing for 1 minute at 65-72° C. |
| step 7 | repeating steps 5 and 6 for 5-35 circles |
| step 8 | extending for 5 minutes at 72° C. |

Therefore, the GC bias during PCR amplification is low, the amplification specificity is high and the amplification effect is excellent.

In a fourth aspect, the present disclosure in embodiments provides a method for preparing a circular DNA library. According to embodiments of the present disclosure, the method comprises the steps of:

(1) subjecting a DNA sample to be tested to PCR amplification according to the method for PCR amplification as described above, so as to obtain an amplification product comprising a loop-like substance, in which the 5' end and the 3' end of the loop-like substance are not connected, at least one of the first primer and the second primer is subjected to phosphorylation modification at the 5' end, the 1-5$^{th}$ bases from each of the 5' end and the 3' end of the first primer are respectively subjected to thio-modification, the 1-5$^{th}$ bases from each of the 5' end and the 3' end of the second primer are respectively subjected to thio-modification, and (2) subjecting the amplification product comprising the loop-like substance to a ligation reaction by using a ligase, such that the 5' end and the 3' end of the loop-like substance are ligated, thus forming circular DNAs, the circular DNAs constituting the circular DNA library, in which the circular DNA library is a single-stranded circular DNA library when either of the first primer and the second primer is subjected to phosphorylation modification at the 5' end; and the circular DNA library is a double-stranded circular DNA library when both the first primer and the second primer are subjected to phosphorylation modification at the 5' end.

According to embodiments of the present disclosure, a single-stranded circular DNA library or a double-stranded circular DNA library can be efficiently prepared through the method. The obtained single-stranded circular DNA library or double-stranded circular DNA library is of good library quality, which exhibits good effect for DNA preservation or library sequencing.

According to embodiments of the present disclosure, the method further comprises: (3) removing linear DNAs. Thus, the obtained library is of good quality.

According to some specific examples of the present disclosure, the linear DNAs are removed through a linear-chain digestion reaction.

According to embodiments of the present disclosure, the DNA sample to be tested in the step (1) is added with universal sequence at the 5' end and the 3' end respectively. As described above, the expression "universal sequence" used herein means a sequence paired with the specific sequence of the PCR prime pair, including an adaptor sequence for a sequencing platform, i.e. a sequencing adaptor. Thus, the obtained library can be directly used in on-line sequencing on a corresponding sequencing platform, when the DNA sample to be tested is added with the universal sequence such as a sequencing adaptor at two ends respectively.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang P T), *Molecular Cloning: A Laboratory Manual*, 3rd Ed., Science Press) or in accordance with the product instructions. If the manufacturers of reagents or instruments are not specified, the reagents or instruments may be conventional products that are commercially available, for example, from Illumina Company.

Example 1: Padlock Primer Improves Specificity and Amplification Efficiency Relative to Conventional Primer 1.1 Primer Design of Padlock Primer (i.e. PCR Primer Pair of the Present Disclosure, Referred to as "PP Primer" Below)

1.1.1 A conventional primer pair was designed through NC_000004.12 (*Homo sapiens* chromosome 4, GRCh38.p7 Primary Assembly), with an amplified product in a length of 277 bp. The conventional primer pair was added with complementary sequences of 24 bp, 19 bp and 11 bp at the 5' end respectively, thus obtaining three padlock primer pairs.

1.1.2 Five conventional primer pairs (respectively having amplified products in a length of 88 bp, 235 bp, 318 bp, 404 bp and 498 bp) were designed through NC_000016.10 (*Homo sapiens* chromosome 16, GRCh38.p7 Primary Assembly), which were each added with a 18 bp of complementary sequence at the 5' end, thus obtaining five padlock primer pairs, referring to Table 1 and FIG. 1 showing the schematic primer structure.

1.2 Experimental Steps

For each of 6 conventional primer pairs and 8 padlock primer pairs (primer sequences referring to Table 1), 10 ng of genomic DNAs were taken for PCR amplification by using the rTaq amplification kit from Takara (Catalog No: RR001B) according to the amplification system shown in the following table:

| | |
|---|---|
| rTaq Buffer (10X) | 2 μL |
| Genomic DNA | 16.3 μL |
| Forward primer (10 μM) | 0.5 μL |
| Reverse primer (10 μM) | 0.5 μL |
| dNTP Mixture | 0.5 μL |
| rTaqDNA Polymerase | 0.2 μL |
| Total | 20 μL |

A) The amplification conditions for conventional primers were as follows:

| | |
|---|---|
| Step 1 | 98° C., 2 minutes |
| Step 2 | 98° C., 10 seconds |
| Step 3 | 58° C., 2 minutes |
| Step 4 | 72° C., 30 seconds |
| Step 5 | repeating steps 3 and 4 for 30 cycles |
| Step 8 | 72° C., 5 minutes |

B) The amplification conditions for PP primers were as follows:

| | |
|---|---|
| Step 1 | 98° C., 2 minutes |
| Step 2 | 98° C., 10 seconds |
| Step 3 | 58° C., 2 minutes |
| Step 4 | 72° C., 30 seconds |
| Step 5 | 98° C., 10 seconds |
| Step 6 | 68° C., 1 minute |
| Step 7 | repeating steps 5 and 6 for 29 cycles |
| Step 8 | 72° C., 5 minutes |

Figure 5:
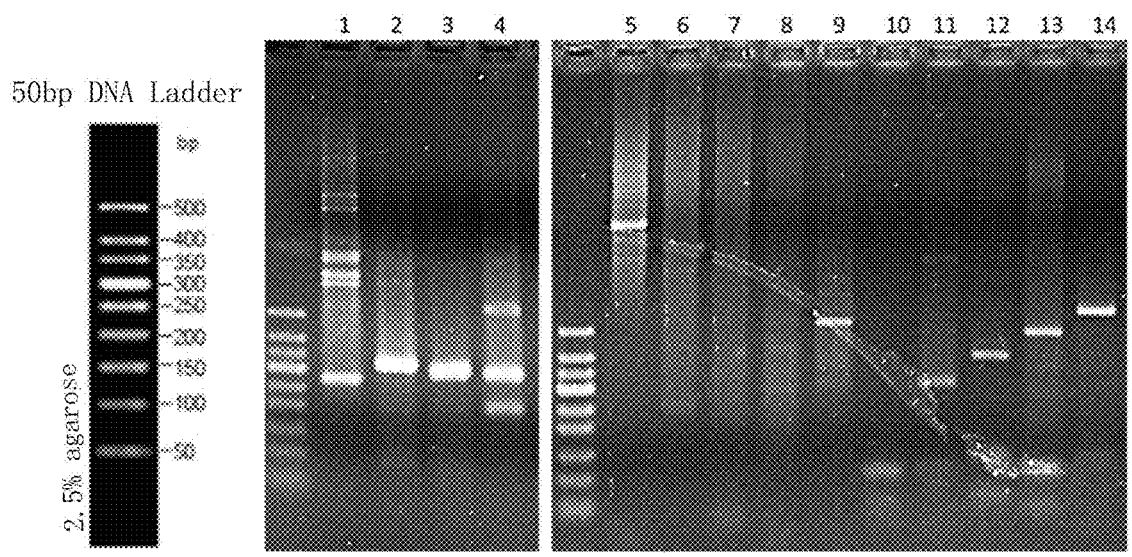
FIG. 5 is a graph showing detection results of agarose gel electrophoresis of PCR amplification products obtained by using padlock primers in Example 1.
Figure 6:
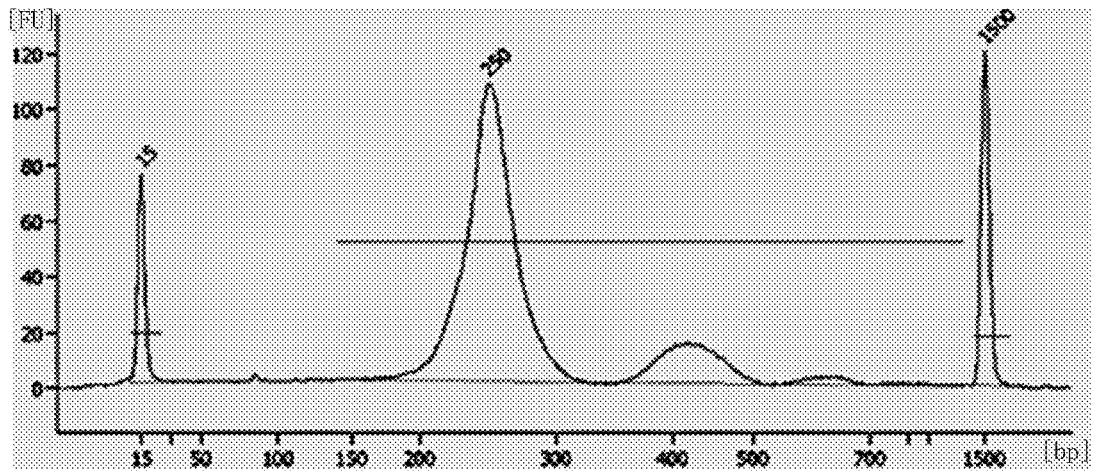
FIGS. 6 to 9 are graphs showing 2100 electrophoresis detection results of different types of libraries obtained in Example 2, in which, FIGS. 6 to 9 respectively represent the 2100 electrophoresis detection results of cfDNA library of conventional primer, cfDNA library of padlock primer, *E. coli* genomic library of conventional primer and *E. coli* genomic library of padlock primer.
Figure 7:
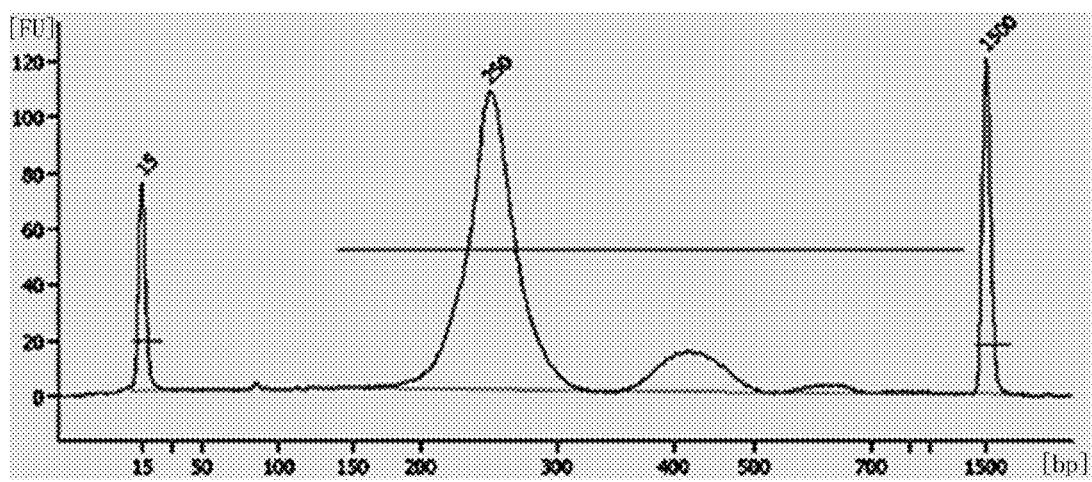
Figure 8:
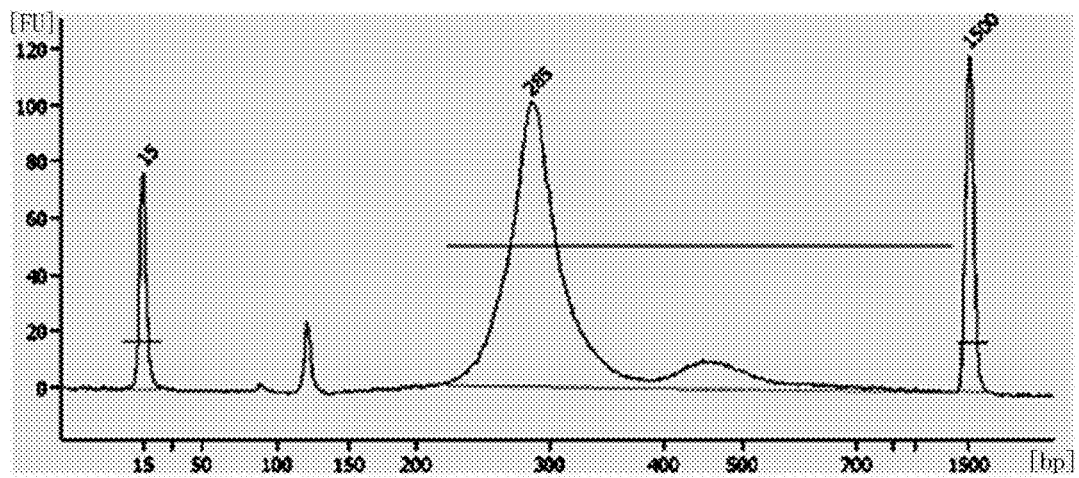
Figure 9:
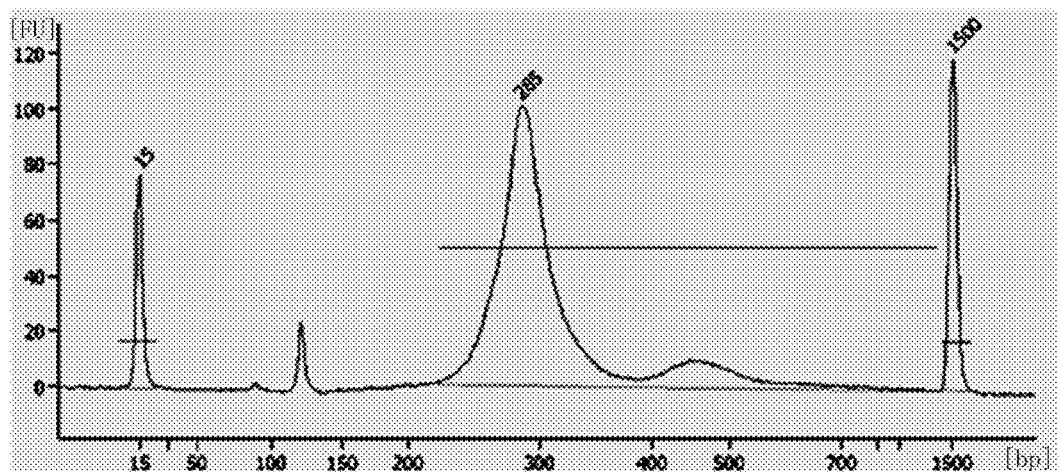

1.2.1 The resulting products were subjected to purification and agarose gel electrophoresis, refer to FIG. 5.

TABLE 1

Primer sequences

| Primer Nos. | Primer name | Sequences (5'-3', SEQ ID NO:) | Length |
|---|---|---|---|
| 1 | Control-F | GCTCTGGGGGCTCGGCTT (1) | 277 bp |
| | Control-R | AACGCACGGGCACTGAGG (2) | |
| 2 | PP-24BP-F | GCGGGCGGTTGGCCGGCGCGCGGC GCTCTGGGGGCTCGGCTT (3) | 325 bp (24 bp of |
| | PP-24BP-R | GCCGCGCGCCGGCCAACCGCCCGC AACGCACGGGCACTGAGG (4) | complementary sequence) |
| 3 | PP-19BP-F | GCGGGCGGTTGGCCGGCGG CTCTGGGGGCTCGGCTT (5) | 315 bp (19 bp of |
| | PP-19BP-F | CGCCGGCCAACCGCCCGCA ACGCACGGGCACTGAGG (6) | complementary sequence) |
| 4 | PP-11BP-F | GGGGGGGGGGG CTCTGGGGGCTCGGCTT (7) | 299 bp (11 bp of |
| | PP-11BP-R | CCCCCCCCCCC ACGCACGGGCACTGAGG (8) | complementary sequence) |
| 5 | Control-1F | CCTTACGGATAGTATAACATAAAGTC (9) | 88 bp |
| | Control-1R | GACAGAGCGAGACTCCGT (10) | |
| 6 | Control-2F | TCCCGAGTAGCTGGGACT (11) | 235 bp |
| | Control-2R | TCTTTCTTATCTCCTCCAATGATCT (12) | |
| 7 | Control-3F | TACCACGCCCGGCTAATTTTTTGTA (13) | 318 bp |
| | Control-3R | TATGGCTATCTGGTCCCAACATAATT (14) | |
| 8 | Control-4F | GATCTCCTGACCTCGTGATC (15) | 404 bp |
| | Control-4R | TGAAGGCTAATCCTAAGAGCTGAT (16) | |

TABLE 1-continued

Primer sequences

| Primer Nos. | Primer name | Sequences (5'-3', SEQ ID NO:) | Length |
|---|---|---|---|
| 9 | Control-5F | AGAATTTAGCACGATAAAGAGAGCA(17) | 498 bp |
|   | Control-5R | CTGGAGTGCAATGGCCTG(18) |  |
| 10 | PP-F1 | ⌐GCGCGGCCAAGCCGGGCG¬CCTTACGGATAGTATAACATAAAGTC(19) | 124 bp |
|    | PP-R1 | ⌐CGCCCGGCTTGGCCGCGG¬GACAGAGCGAGACTCCGT(20) |  |
| 11 | PP-F2 | ⌐GGCGCCCGAAGGCCCGCG¬TCCCGAGTAGCTGGGACT(21) | 271 bp |
|    | PP-R2 | ⌐CGCGGGCCTTCGGGCGCC¬TCTTTCTTATCTCCTCCAATGATCT(22) |  |
| 12 | PP-F3 | ⌐CCGCCGGCTAGCCCGCCG¬TACCACGCCCGGCTAATTTTTTGTA(23) | 354 bp |
|    | PP-R3 | ⌐CGGCGGGCTAGCCGGCGG¬TATGGCTATCTGGTCCCAACATAATT(24) |  |
| 13 | PP-F4 | ⌐CGCCGCGCATGCCGCCGG¬GATCTCCTGACCTCGTGATC(25) | 440 bp |
|    | PP-R4 | ⌐CCGGCGGCATGCGCGGCG¬TGAAGGCTAATCCTAAGAGCTGAT(26) |  |
| 14 | PP-F5 | ⌐CCCCGCGCTACCGCCCCG¬AGAATTTAGCACGATAAAGAGAGCA(27) | 534 bp |
|    | PP-R5 | ⌐CGGGGCGGTAGCGCGGGG¬CTGGAGTGCAATGGCCTG(28) |  |

Note:
F: Forward primer; R: Reverse primer; Control: Conventional primer; PP: Padlock primer; and the complementary sequence of each PP primer is highlighted in box.

FIG. 5 shows the detection results of agarose gel electrophoresis of PCR amplification products obtained by padlock primers. As shown in FIG. 5, bands 1, 2, 3 and 4 respectively represent amplification products of a conventional primer pair, a padlock primer pair with 24 bp of complementary sequence, a padlock primer pair with 19 bp of complementary sequence, and a padlock primer pair with 11 bp of complementary sequence, with expected length of 277 bp, 325 bp, 315 bp and 299 bp respectively. Among them, band 4 was obtained in the presence of primers PP-11BP-F and PP-11BP-R, that is, representing the amplification product of the padlock primer pair with 11 bp of complementary sequence, however, showing a poor amplification effect, thus the present inventors limited the minimum length of the complementary sequence to be 15 bp. Bands 5-9 represent amplification products of conventional primers, with expected length of 88 bp, 235 bp, 318 bp, 404 bp and 498 bp. Bands 10-14 represent amplification products of the padlock primer pairs with 18 bp of complementary sequence, with expected length of 124 bp, 271 bp, 354 bp, 440 bp and 534 bp.

Conclusion: it can be seen from FIG. 5 that conventional primers result in severe non-specific amplification; in contrast, the padlock primers of different lengths (within the length from 15 bp to 45 bp) exhibit significant improvement on amplification, in which longer the complementary sequence is, better specificity gets. Thus, the amplification specificity of primer is greatly improved through the padlock primer-related strategy.

Example 2: Application of Padlock Primers in Enrichment of BGI-SEQ500 Library

Figure 2:
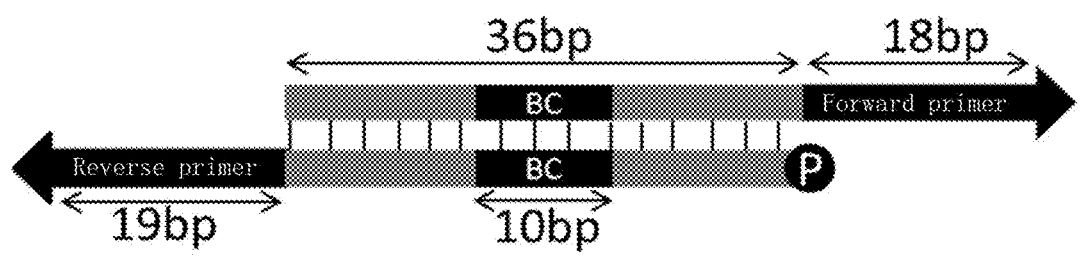
FIG. 2 is a schematic diagram showing the structure of a PCR primer pair (i.e. a padlock primer) of the present disclosure according to another embodiment of the present disclosure.

In this example, conventional primers and padlock primers of the present disclosure (refer to FIG. 2, showing the schematic structure) were respectively used to prepare libraries for *E. coli* genomic DNA and cell-free DNA (i.e. cfDNA) as a template.

Figure 4:
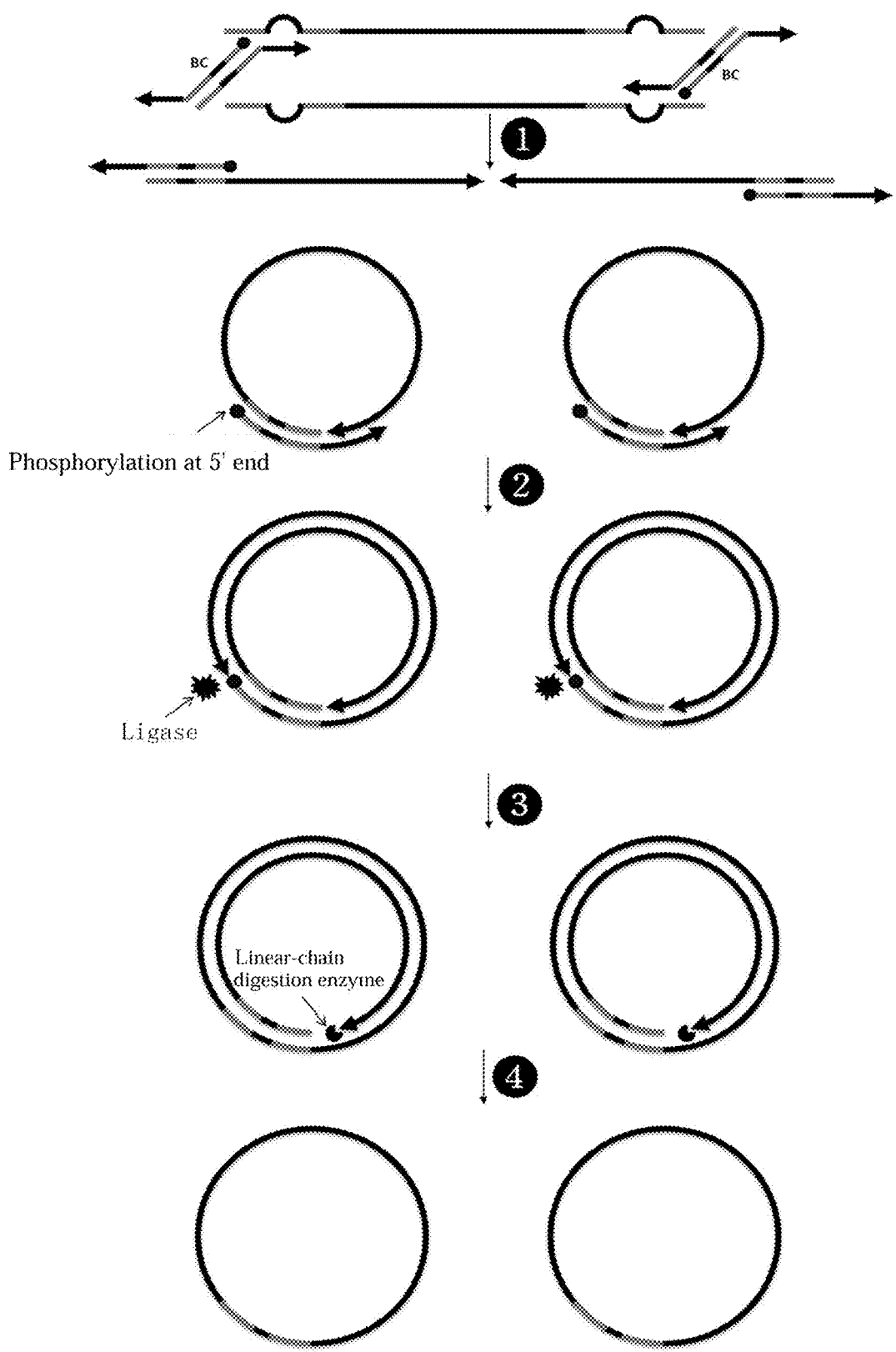
FIG. 4 is a schematic flow chart showing preparation of a BGISEQ-500 library by using a PCR primer pair of the present disclosure according to an embodiment of the present disclosure, in which markers respectively represent 1—first round of linear PCR amplification; 2—second round of circular PCR amplification; 3—Ligation reaction; and 4—Linear digestion.

10 ng of taken *E. coli* genomic DNA and 2 ng of extracted cfDNA were respectively fragmented into about 200 bp of fragments by Cavoris, followed by library construction by using the combined probe anchored polymerization sequencing kit from BGI (Catalog No. BOX3) through the following steps. FIG. 4 shows the flow chat for library construction.

2.1 Terminal Repairing and Adenine (A) Addition

Terminal repairing and adenine (A) addition for library construction were as follows:

| DNA | 40 μL |
|---|---|
| Buffer | 9.4 μL |
| Enzyme | 0.6 μL |
| Total | 50 μL |

Reaction conditions were 37° C. for 30 minutes and 65° C. for 15 minutes.

DNAs: *E. coli* genomic DNA or cell-free DNA (cfDNA).

2.2 Adaptor Ligation

The ligation system was as follows:

| Terminal-repaired DNA | 50 μL |
|---|---|
| DNA ligase | 1 μL |
| Ligation buffer | 24 μL |
| Adaptor | 5 μL |
| Total | 80 μL |

Reaction condition was 23° C. for 30 minutes.

2.3 Library Enrichment

The PCR amplification system was as follows:

| 2 × kapa HIFI master mix | 25 μL |
|---|---|
| DNA-ligated product | 21 μL |

-continued

| | |
|---|---|
| Primer 1 (10 μM) | 2 μL |
| Primer 2 (10 μM) | 2 μL |
| Total | 50 μL |

The primer sequences are shown in Table 2:

TABLE 2

| Primer name | Sequences (5'-3', SEQ ID NO:) |
|---|---|
| Primer 1 | GAAGACAA*GTCCAAACAG*CAACTCCTTGGCTCACAGAACGACATGGCTACGATC(29) |
| Primer 2 | TGTGAGCCAAGGAGTTG*CTGTTTGGAC*TTGTCTTCCTAAGACCGCTTGGCCTC(30) |

Note:
the bases underlined are tag sequence.

PCR reaction conditions were as follows:

| | |
|---|---|
| Step 1 | 98° C., 2 minutes |
| Step 2 | 98° C., 10 seconds |
| Step 3 | 58° C., 1 minute |
| Step 4 | 72° C., 30 seconds |
| Step 5 | 98° C., 10 seconds |
| Step 6 | 68° C., 1 minute |
| Step 7 | repeating steps 5 and 6 for 5-15 cycles |
| Step 8 | 72° C., 5 minutes |

2.4 Library Cyclization
Cyclization reaction system was as follows:

| | |
|---|---|
| PCR product | 50 μL |
| 10 × TA buffer | 6 μL |
| T4DNA ligase | 4 μL |
| Total | 60 μL |

Reaction condition was 37° C. for 30 minutes.

2.5 The ligation products were subjected to purification followed by qubit quantification (refer to Table 3) and 2100 Bioanalyzer detection (refer to FIGS. 6-9).

2.6 The qualified library was subjected to on-machine sequencing by using BGISEQ-500 sequencing platform and the sequencing type of SE28+10. The basic parameters of off-machine data including GC bias, aligning rate, repetitive rate and the like were subjected to statistics analysis (refer to Table 4 and FIGS. 10-11).

FIGS. 6 to 9 show the 2100 electrophoresis detection results of different types of libraries obtained, including cfDNA library of conventional primer, cfDNA library of padlock primer, E. coli genomic library of conventional primer and E. coli genomic library of padlock primer.

TABLE 3

Library output

| Types | Input (ng) | Output (ng) |
|---|---|---|
| cfDNA library of conventional primer | 2 | 430 |
| cfDNA library of padlock primer | 2 | 640 |
| E. coli genomic library of conventional primer | 10 | 1560 |
| E. coli genomic library of padlock primer | 10 | 2600 |

TABLE 4

Statistics of library off-machine data

| Types | Original data (reads) | Alignment rate | Unique Hit Rate | Repetitive rate | Mismatch rate |
|---|---|---|---|---|---|
| cfDNA library of conventional primer | 6525963 | 92.1% | 97.5% | 0.1% | 0.5% |
| cfDNA library of padlock primer | 6635893 | 93.4% | 97.3% | 0.2% | 0.3% |
| E. coli genomic library of conventional primer | 2278185 | 97.5% | 97.5% | 23.3% | 0.4% |
| E. coli genomic library of padlock primer | 2242635 | 97.7% | 97.1% | 20.6% | 0.6% |

Figure 10:
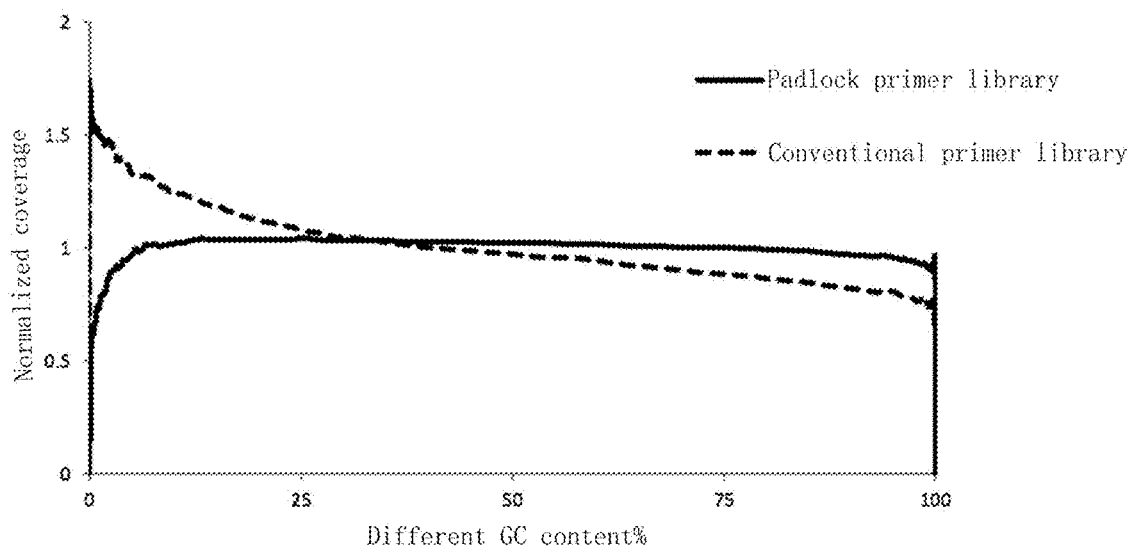
FIGS. 10 and 11 are graphs showing detection results of GC bias of different types of libraries in Example 2.
Figure 11:
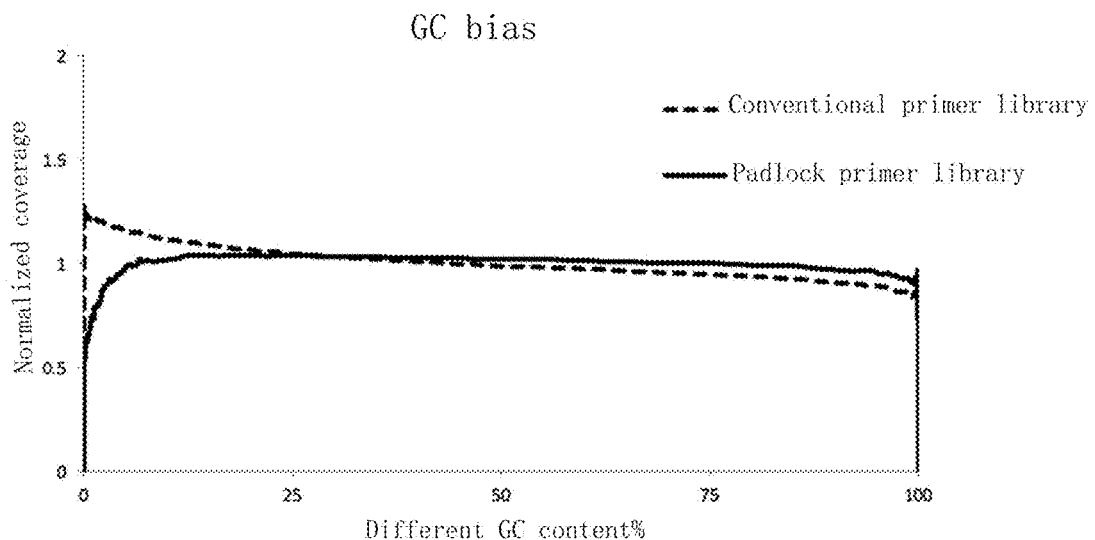

FIGS. 10 and 11 show detection results of GC bias for different types of libraries, in which in FIG. 10, the dotted line represents GC bias of conventional primer and the solid line represents GC bias of padlock primer, indicating less fluctuation with change of GC content for the library depth obtained by the padlock primer; and in FIG. 11, the dotted line represents GC bias of conventional primer and the solid line represents GC bias of padlock primer, indicating less fluctuation with change of GC content for the library depth obtained by the padlock primer, thus the results demonstrate that the padlock primer can effectively improve GC bias.

Conclusion: it can be seen from Table 3 and FIGS. 6-9 that the library output of padlock primers has been improved significantly, indicating that padlock primers can improve the efficiency of PCR amplification; and Table 4 and FIGS. 10-11 show that the off-machine data (for example, basic parameters such as alignment rate) of padlock primers are not different from conventional primers apparently, however, the padlock primers can effectively improve the GC bias of library compared to conventional primers. The padlock primer can be applied for library construction not only on the BGISEQ-500 sequencing platform but only on other next-generation sequencing platforms such as illumina, proton and the like.

INDUSTRIAL APPLICABILITY

The PCR primer pair of the present disclosure can be effectively used for PCR amplification of DNA samples to be tested, effectively reduce GC bias during PCR amplification, and improve amplification specificity.

Although specific embodiments of the present disclosure have been described in detail, it would be appreciated by those skilled in the art that various modifications and alternatives of the details can be made according to teachings of the present disclosure, which are all within the scope of the present disclosure. The full scope of the present disclosure is given by the appended claims and any equivalents thereof.

Reference throughout this specification to terms "an embodiment", "some embodiments", "illustrative embodiment", "an example", "a specific example" or "some examples" means that a particular feature, structure, material, or characteristic described in connection with the embodiment or example is included in at least one embodiment or example of the present disclosure. Thus, the description with reference to the terms "an embodiment", "some embodiments", "illustrative embodiment", "an example", "a specific example" or "some examples" throughout this specification are not necessarily referring to the same embodiment or example of the present disclosure. Furthermore, the particular features, structures, materials, or characteristics may be combined in any suitable manner in one or more embodiments or examples.

The invention claimed is:

1. A method for nucleic acid amplification, comprising:
performing amplification by using a primer pair comprising a first primer and a second primer, wherein the first primer comprises a first specific sequence and a first random sequence, and the second primer comprises a second specific sequence and a second random sequence,
wherein the first specific sequence is located at the 3' end of the first primer and the first random sequence is located at the 5' end of the first primer, the second specific sequence is located at the 3' end of the second primer and the second random sequence is located at the 5' end of the second primer, the first specific sequence and the second specific sequence are respectively an upstream primer and a downstream primer for a template sequence, and the first random sequence and the second random sequence are reversely complementary,
wherein the amplification comprises two rounds, wherein the first round of amplification is performed at a first annealing temperature, and the second round of amplification is performed at a second annealing temperature that is higher than the first annealing temperature so as to obtain a circular product.

2. The method according to claim 1, wherein in the first round of amplification, the primer pair and the template sequence are subjected to amplification under an annealing temperature of 55-65° C., and in the second round of amplification, a product of the first round of amplification is subjected to amplification under an annealing temperature of 65-72° C.

3. The method according to claim 1, wherein the two rounds of amplification are performed as the following amplification reaction procedure:

| | |
|---|---|
| step 1 | preheating for 2 minutes at 98° C. |
| step 2 | denaturing for 10 seconds at 98° C. |
| step 3 | annealing for 2 minutes at 55-65° C. |
| step 4 | amplifying for 30 seconds at 72° C. |
| step 5 | denaturing for 10 seconds at 98° C. |
| step 6 | annealing for 1 minute at 65-72° C. |
| step 7 | repeating steps 5 and 6 for 5-35 circles |
| step 8 | extending for 5 minutes at 72° C. |

4. A method for preparing a circular DNA library, comprising the steps of:
(1) subjecting a DNA sample comprising template sequences to the method of claim 1, so as to obtain circular amplification products, wherein the circular amplification products are double-stranded, wherein each strand of each double stranded circular amplification product comprises a 5' end and a 3' end, wherein the 5' end and the 3' end of each strand of each double-stranded circular amplification product are not connected, wherein at least one of the first primer and the second primer used in the amplification is phosphorylated at the 5' end, wherein the 1-5th bases from each of the 5' end and the 3' end of the first primer respectively contain thio-modifications, wherein the 1-5th bases from each of the 5' end and the 3' end of the second primer respectively contain thio-modifications, and (2) subjecting the double-stranded circular amplification products to a ligation reaction by using a ligase, such that the 5' end and the 3' end of at least one strand of the double-stranded circular amplification products are ligated, thus forming ligated circular DNAs, the ligated circular DNAs constituting the circular DNA library, wherein the circular DNA library is a single-stranded circular DNA library when only one of the first primer and the second primer is phosphorylated at the 5' end; and the circular DNA library is a double stranded circular DNA library when both the first primer and the second primer are phosphorylated at the 5' end.

5. The method according to claim 4, further comprising: (3) removing unligated DNAs having 5' and 3' ends.

6. The method according to claim 5, wherein the linear unligated DNAs having 5' and 3' ends are removed by digestion.

7. The method according to claim 4, wherein in step (1), the DNA molecules of the sample to be tested are modified with universal sequences at the 5' end and the 3' end respectively.

8. The method according to claim 1, wherein the first specific sequence and the second specific sequence each have a TM value of 55-65° C., and the first primer and the second primer each have a TM value of 65-75° C.

9. The method according to claim 1, wherein the first round of amplification comprises: subjecting the primer pair and the template sequence to amplification under an annealing temperature of 55-65° C. so as to obtain a linear product; and the second round of amplification comprises: subjecting the primer pair and the linear product to amplification under an annealing temperature of 65-72° C. so as to obtain the circular product.

10. The method according to claim 1, wherein the first round of amplification further comprises:

subjecting the first specific sequence of the first primer to binding to the upstream of the template sequence, and subjecting the second specific sequence of the second primer to binding to the downstream of the template sequence, so as to obtain linear products; and the second round of amplification further comprises:

subjecting a second molecule of the first primer to binding to a linear product of the first round of amplification, wherein the first random sequence of the second molecule of the first primer binds to a 5' end of the linear product, and the first specific sequence of the second molecule of the first primer binds to a 3' end of the linear product, and subjecting a second molecule of the second primer to binding to a linear product of the first round of amplification, wherein the second random sequence of the second molecule of the second primer binds to a 5' end of the linear product, and the second specific sequence of the second molecule of the second primer binds to a 3' end of the linear product, so as to obtain the circular products of the second round of amplification.

11. The method according to claim 1, wherein in the second round of amplification, the first random sequence of a first primer and the second random sequence of a second primer bind to 5' ends of products from the first round of amplification, and the first specific sequence of a first primer and the second specific sequence of a second primer bind to 3' ends of products from the first round of amplification.

12. The method according to claim 1, further comprising: subjecting the circular product to a ligation reaction by using a ligase, such that a 5' end and a 3' end of the circular product are ligated, thus forming a ligated circular product.

13. The method according to claim 1, wherein the first random sequence and the second random sequence each have a length of 15-45 nucleotides, and the first specific sequence and the second specific sequence each have a length of 15-30 nucleotides.

14. The method according to claim 1, wherein the 1-5th bases from each of the 5' end and the 3' end of the first primer comprise modifications, and the 1-5th bases from each of the 5' end and the 3' end of the secondary primer comprise modifications.

15. The method according to claim 14, wherein the modifications are selected from phosphorothioate modifications, methyl-sulfate modifications and peptide nucleic acid modifications.

16. The method according to claim 1, wherein at least one of the first primer and the second primer is phosphorylated at the 5' end.

* * * * *

SEQUENCE LISTING

<160> NUMBER OF SEQ ID NOS: 30

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
gctctggggg ctcggctt                                                   18

<210> SEQ ID NO 2
<211> LENGTH: 18
<212> TYPE: DNA
<213> ORGANISM: Artificial
<220> FEATURE:
<223> OTHER INFORMATION: Primer

<400> SEQUENCE: 2
aacgcacggg cactgagg                                                   18

<210> SEQ ID NO 3
<211> LENGTH: 42
<212> TYPE: DNA
<213> ORGANISM: Artificial
<220> FEATURE:
<223> OTHER INFORMATION: Primer

<400> SEQUENCE: 3
gcgggcggtt ggccggcgcg cggcgctctg ggggctcggc tt                        42

<210> SEQ ID NO 4
<211> LENGTH: 42
<212> TYPE: DNA
<213> ORGANISM: Artificial
<220> FEATURE:
<223> OTHER INFORMATION: Primer

<400> SEQUENCE: 4
gccgcgcgcc ggccaaccgc ccgcaacgca cgggcactga gg                        42

<210> SEQ ID NO 5
<211> LENGTH: 36
<212> TYPE: DNA
<213> ORGANISM: Artificial
<220> FEATURE:
<223> OTHER INFORMATION: Primer

<400> SEQUENCE: 5
gcgggcggtt ggccggcggc tctgggggct cggctt                               36

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6
cgccggccaa ccgcccgcaa cgcacgggca ctgagg                               36

<210> SEQ ID NO 7
<211> LENGTH: 28
<212> TYPE: DNA
<213> ORGANISM: Artificial

```
<220> FEATURE:
<223> OTHER INFORMATION: Primer

<400> SEQUENCE: 7
gggggggggg gctctggggg ctcggctt                                          28

<210> SEQ ID NO 8
<211> LENGTH: 28
<212> TYPE: DNA
<213> ORGANISM: Artificial
<220> FEATURE:
<223> OTHER INFORMATION: Primer

<400> SEQUENCE: 8
cccccccccc aacgcacggg cactgagg                                          28

<210> SEQ ID NO 9
<211> LENGTH: 26
<212> TYPE: DNA
<213> ORGANISM: Artificial
<220> FEATURE:
<223> OTHER INFORMATION: Primer

<400> SEQUENCE: 9
ccttacggat agtataacat aaagtc                                            26

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
gacagagcga gactccgt                                                     18

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
tcccgagtag ctgggact                                                     18

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
tctttcttat ctcctccaat gatct                                             25

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
taccacgccc ggctaatttt ttgta                                             25
```

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
tatggctatc tggtcccaac ataatt                                   26

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
gatctcctga cctcgtgatc                                          20

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
tgaaggctaa tcctaagagc tgat                                     24

<210> SEQ ID NO 17
<211> LENGTH: 25
<212> TYPE: DNA
<213> ORGANISM: Artificial
<220> FEATURE:
<223> OTHER INFORMATION: Primer

<400> SEQUENCE: 17
agaatttagc acgataaaga gagca                                    25

<210> SEQ ID NO 18
<211> LENGTH: 18
<212> TYPE: DNA
<213> ORGANISM: Artificial
<220> FEATURE:
<223> OTHER INFORMATION: Primer

<400> SEQUENCE: 18
ctggagtgca atggcctg                                            18

<210> SEQ ID NO 19
<211> LENGTH: 44
<212> TYPE: DNA
<213> ORGANISM: Artificial
<220> FEATURE:
<223> OTHER INFORMATION: Primer

<400> SEQUENCE: 19
gcgcggccaa gccgggcgcc ttacggatag tataacataa agtc               44

<210> SEQ ID NO 20
<211> LENGTH: 36
<212> TYPE: DNA
<213> ORGANISM: Artificial
<220> FEATURE:
<223> OTHER INFORMATION: Primer

<400> SEQUENCE: 20
cgcccggctt ggccgcgcga cagagcgaga ctccgt                                36

<210> SEQ ID NO 21
<211> LENGTH: 36
<212> TYPE: DNA
<213> ORGANISM: Artificial
<220> FEATURE:
<223> OTHER INFORMATION: Primer

<400> SEQUENCE: 21
ggcgcccgaa ggcccgcgtc ccgagtagct gggact                                36

<210> SEQ ID NO 22
<211> LENGTH: 43
<212> TYPE: DNA
<213> ORGANISM: Artificial
<220> FEATURE:
<223> OTHER INFORMATION: Primer

<400> SEQUENCE: 22
cgcgggcctt cgggcgcctc tttcttatct cctccaatga tct                        43

<210> SEQ ID NO 23
<211> LENGTH: 43
<212> TYPE: DNA
<213> ORGANISM: Artificial
<220> FEATURE:
<223> OTHER INFORMATION: Primer

<400> SEQUENCE: 23
ccgccggcta gcccgccgta ccacgcccgg ctaatttttt gta                        43

<210> SEQ ID NO 24
<211> LENGTH: 44
<212> TYPE: DNA
<213> ORGANISM: Artificial
<220> FEATURE:
<223> OTHER INFORMATION: Primer

<400> SEQUENCE: 24
cggcgggcta gccggcggta tggctatctg gtcccaacat aatt                       44

<210> SEQ ID NO 25
<211> LENGTH: 38
<212> TYPE: DNA
<213> ORGANISM: Artificial
<220> FEATURE:
<223> OTHER INFORMATION: Primer

<400> SEQUENCE: 25
cgccgcgcat gccgccggga tctcctgacc tcgtgatc                              38

<210> SEQ ID NO 26
<211> LENGTH: 42
<212> TYPE: DNA
<213> ORGANISM: Artificial
<220> FEATURE:
<223> OTHER INFORMATION: Primer

<400> SEQUENCE: 26
ccggcggcat gcgcggcgtg aaggctaatc ctaagagctg at                         42

```
<210> SEQ ID NO 27
<211> LENGTH: 43
<212> TYPE: DNA
<213> ORGANISM: Artificial
<220> FEATURE:
<223> OTHER INFORMATION: Primer

<400> SEQUENCE: 27
ccccgcgcta ccgccccgag aatttagcac gataaagaga gca                  43

<210> SEQ ID NO 28
<211> LENGTH: 36
<212> TYPE: DNA
<213> ORGANISM: Artificial
<220> FEATURE:
<223> OTHER INFORMATION: Primer

<400> SEQUENCE: 28
cggggcggta gcgcggggct ggagtgcaat ggcctg                          36

<210> SEQ ID NO 29
<211> LENGTH: 54
<212> TYPE: DNA
<213> ORGANISM: Artificial
<220> FEATURE:
<223> OTHER INFORMATION: Primer

<400> SEQUENCE: 29
gaagacaagt ccaaacagca actccttggc tcacagaacg acatggctac gatc      54

<210> SEQ ID NO 30
<211> LENGTH: 53
<212> TYPE: DNA
<213> ORGANISM: Artificial
<220> FEATURE:
<223> OTHER INFORMATION: Primer

<400> SEQUENCE: 30
tgtgagccaa ggagttgctg tttggacttg tcttcctaag accgcttggc ctc       53
```